United States Patent [19]
Lo Duca

[11] Patent Number: 5,116,320
[45] Date of Patent: May 26, 1992

[54] DISPOSABLE SYRINGE FOR ONCE-ONLY USE

[75] Inventor: Carmelo Lo Duca, Milan, Italy

[73] Assignee: GI.BI.EFFE S.R.L., Milan, Italy

[21] Appl. No.: 770,160

[22] Filed: Oct. 3, 1991

Related U.S. Application Data

[63] Continuation of Ser. No. 538,095, Jun. 13, 1990, abandoned.

[30] Foreign Application Priority Data

Jul. 5, 1989 [IT] Italy .............................. 21108 A/89

[51] Int. Cl.⁵ .............................................. A61M 5/00
[52] U.S. Cl. ....................................... 604/110; 128/919
[58] Field of Search ............... 604/110, 227, 214, 264, 604/107, 199, 218, 221, 220, 224, 187; 228/919

[56] References Cited

U.S. PATENT DOCUMENTS

| | | |
|---|---|---|
| 3,478,937 | 11/1969 | Solowey ................................ 604/110 |
| 3,667,657 | 6/1972 | Chiquiar-Arias .................... 222/541 |
| 3,934,586 | 1/1976 | Easton et al. . |
| 3,951,146 | 4/1976 | Chiquiar-Arias .................... 128/218 |
| 3,967,759 | 7/1976 | Baldwin et al. ................. 604/218 X |
| 3,998,224 | 12/1976 | Chiquiar-Arias .................... 128/218 |
| 4,121,588 | 10/1978 | Geiger ................................... 128/218 |
| 4,233,975 | 11/1980 | Yerman ................................ 604/110 |
| 4,391,272 | 6/1983 | Staempfli . |
| 4,439,184 | 3/1984 | Wheeler ................................. 604/90 |
| 4,571,242 | 2/1986 | Klein et al. ........................... 604/111 |
| 4,699,614 | 10/1987 | Glazier . |
| 4,781,684 | 11/1988 | Trenner ......................... 604/218 X |
| 4,863,072 | 9/1989 | Perler ................................... 604/227 |

FOREIGN PATENT DOCUMENTS

| | | |
|---|---|---|
| 0307367 | 3/1989 | European Pat. Off. ............ 604/110 |
| 0325886 | 8/1989 | European Pat. Off. . |
| 0364839 | 4/1990 | European Pat. Off. . |
| 0385153 | 5/1990 | European Pat. Off. . |
| 7215412 | 12/1973 | France . |
| 2298340 | 9/1976 | France ............................... 604/110 |
| 2622804 | 5/1989 | France . |
| 2622809 | 5/1989 | France ............................... 604/110 |
| 2117249 | 10/1983 | United Kingdom . |
| 2197792 | 6/1988 | United Kingdom . |
| 2205750 | 12/1988 | United Kingdom . |

*Primary Examiner*—C. Fred Rosenbaum
*Assistant Examiner*—M. Mendez
*Attorney, Agent, or Firm*—Oblon, Spivak, McClelland, Maier & Neustadt

[57] ABSTRACT

This invention relates to a disposable syringe for once-only use. The syringe includes a hollow cylinder which carries a needle at one end and houses a plunger connected to one end of a shaft, the other end of which is provided with a manually operable shaped head, the diameter of this head is a maximum in proximity to that portion adjacent to the shaft and reduces gradually towards the free end of the head. The shaft length is such that when the plunger has been pushed to the bottom of the cylinder, the maximum diameter portion of the head is housed within the cavity of the cylinder so that the shaft head can no longer be gripped by the fingers in order to move the shaft backwards and reuse the syringe.

4 Claims, 1 Drawing Sheet

DISPOSABLE SYRINGE FOR ONCE-ONLY USE

This application is a continuation of application Ser. No. 07/538,095, filed on Jun. 13, 1990, now abandoned.

BACKGROUND OF THE INVENTION

1. Field of the Invention

This invention relates to a disposable syringe for once-only use, (i.e., is shaped such that it is impossible to move the plunger within the syringe cylinder after said plunger has been once pushed to the bottom of the syringe).

2. Discussion of the Background

There is known to be an increasingly urgent requirement for syringes which can be used once only, (i.e., which are unable to draw in new liquid once the original liquid initially drawn into the syringe has been injected).

This is to prevent the repeated use of syringes and the resultant spread of certain infective illnesses which currently afflict humanity.

The problem has been studied throughout the world and many solutions have been proposed. Some of these are very complex and costly, such as those described in the patents U.S. Pat. No. 4,699,614 and GBP-A-2,205,750.

The patent applications PCT WO 88/10127, GB-A-2,015,883 and EP-A-0,325,886 describe syringes in which the plunger and its operating shaft are only weakly linked together, i.e., can disengage and various expedients are provided to ensure that when the plunger has been pushed to the bottom of the cylinder by the action of the shaft, the shaft disengages from the plunger when the shaft is pulled. The plunger thus remains retained at the bottom of the syringe whereas the shaft can be withdrawn from the cylinder but without any possibility of drawing new liquid into the syringe. To retain the plunger more securely in the cylinder, shaped annular ribs or teeth are provided projecting from the inner surface of the cylinder to oppose any movement of the plunger in the direction of its withdrawal from the syringe needle. Syringes constructed in this manner are very costly, both because of the difficulty of making the weak linkage (but in any event strong enough to allow the initial in-drawing of liquid for the first filling of the syringe) between the plunger and shaft, and because of the problems involved in forming internal elements rigid with the cylinder and able to oppose or block the drawing movement of the plunger.

The British and French patent applications GBP-A-2,117,249 and FR-A-2,181,580 describe syringes in which the plunger is provided with a flexible arched flange the free ends of which slide in contact with the inner surface of the cylinder. The concavity of the flange faces the open free end of the cylinder so that when the plunger is pushed forwards (towards the needle), the flange bends and allows the plunger to slide freely. If an attempt is then made to retract the plunger (by withdrawing it from the needle in order to draw liquid into the syringe), the free edges of the flange rub fiercely against the inner surface of the cylinder, to jam against it and prevent withdrawal of the plunger. It can be seen that this type of system does not even allow the initial filling liquid to be drawn into the syringe, which has to be pre-loaded, (i.e., already filled with the liquid to be injected before the plunger is inserted into the syringe cylinder).

The U.S. Pat. No. 3,934,586 describes a syringe the cylinder of which comprises an internal groove or recess against which a tooth projecting from the syringe and obtained by manually breaking a breakable tab formed integrally with the shaft rests (to thus prevent withdrawal of the shaft). This syringe is also of complex structure and must be pre-filled with the liquid to be injected.

French patent application FR-A-2,622,804 describes a syringe, in the cylinder of which, in proximity to that end at which the hypodermic needle is mounted, there is provided a continuous annular recess into which a shaped elastically flexible portion of the shaft which projects radially outwards becomes inserted in a non-removably manner. To aid in the retention of the shaft against the syringe cylinder when the plunger has been pushed to the bottom of the cylinder, an annular groove can be provided in proximity to the free end of the cylinder, into which the shaft head, in the form of a flat thin disc of shape and dimensions complementary to those of said annular groove, penetrates by snap-insertion. In this manner, when the plunger is pushed to the bottom of the cylinder, the plunger head penetrates totally into the cylinder and can no longer be gripped.

The syringe described in French patent application FR-A-2,622,804 is of truly complicated structure and therefore costly (i.e., due to the presence of the recesses in the cylinder and the corresponding deformable shaped portion of the shaft), whereas the presence of the groove provided in proximity to the free end of the cylinder for snap-housing the disc-shaped head of the shaft is superfluous because engagement between said deformable shaped portion of the shaft and the relative cylinder recesses is already provided for, and it would also be superfluous even if this latter engagement did not exist, because the flat head could be gripped with the finger (in order to withdraw the plunger) up to the point at which the head has been completely pushed into its seat in the cylinder, which means that the syringe would be reusable many times by simply taking care not to push the plunger completely to the bottom of the cylinder. Finally, it can be seen that to push the shaft head right down until it penetrates into the respective locking groove in the cylinder would be very difficult in the case of small syringes (such as insulin syringes), because the finger used to press against the plunger head would rest against the free end of the cylinder, making it impossible to further push the shaft head, as this would be of very small diameter and thickness.

British patent application GB-A-2,197,792 describes a syringe the cylinder of which comprises at its free end a cylindrical sleeve into which the shaft head penetrates completely when the plunger is pushed to the bottom of the cylinder, so that under these conditions the head can no longer be gripped with the fingers to reuse the syringe. Engagement elements can be provided to lock the shaft head in said cylindrical sleeve. The drawback of this syringe is that the shaft head is unable to be gripped with the fingers to reuse the syringe only if this head is pushed completely into the space defined by the cylindrical sleeve, which is difficult to do in the case of a small-dimension syringe, such as syringes used for injecting insulin or for intravenous injections. If the shaft head projects beyond the free edge of the cylindrical sleeve, it can be gripped with the fingers and further liquid can be drawn into the syringe.

SUMMARY OF THE INVENTION

The main object of the present invention is to provide a syringe for once-only use with which liquid can be initially drawn into the syringe and then easily and totally injected into a patient, the plunger and shaft then remaining in the position reached at the end of injection, with the shaft head projecting beyond the free edge of the cylinder but without being able to be gripped and drawn backwards by the fingers because of the tapered elongate shape of said head.

A further object is to provide a syringe of the stated type which is of low production cost, of very simple structure and is reliable and easy to use, even if the syringe is of very small dimensions.

These and further objects are attained by a syringe comprising a hollow cylinder open at one end and connectable to a needle at its other end, and a plunger slidable under sealed conditions within the cylinder and connected to one terminal end of an elongate shaft, the other terminal end of which is rigid with a head operable with a hand finger, characterized in that said head is of elongate form with its cross-section being of varying diameter which is a maximum in proximity to the shaft and is gradually reduced towards the free end of the head, the shaft length being such that when the plunger has been pushed to the bottom of the cylinder, the maximum diameter portion of the head is housed within the cavity of the cylinder, from which the decreasing diameter portion of the head projects.

Preferably, the maximum diameter of the shaft head is slightly greater than the inner diameter of the cylinder, so that said head is under forced fit conditions within the cylinder when pushed into it.

Again preferably, the shaft length is such that the maximum diameter portion of said head is already housed in the cylinder cavity before the plunger has been pushed to the bottom of the cylinder.

BRIEF DESCRIPTION OF THE DRAWINGS

The structure and characteristics of the syringe according to the present invention will be more apparent from the description of two preferred embodiments thereof given by way of non-limiting example with reference to the accompanying drawing, in which.

DESCRIPTION OF THE PREFERRED EMBODIMENTS

Figure 1:
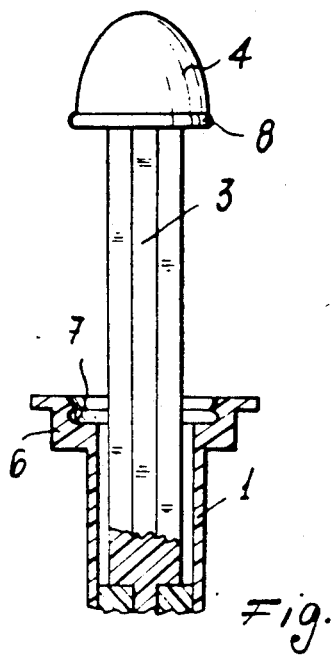
FIG. 1 is a longitudinal sectional view through the portion close to the open free end of a syringe, the shaft being withdrawn from the cylinder into an intermediate operating position.
Figure 2:
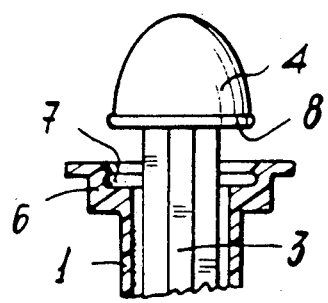
FIG. 2 is a view similar to FIG. 1 but with the shaft inserted to a paint nearly at the end of its downward stroke.
Figure 3:
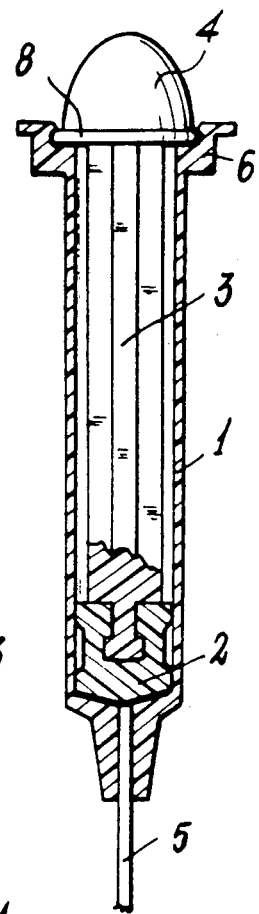
FIG. 3 is a longitudinal sectional view taken through the complete syringe, with the plunger pressed as far as the bottom of the cylinder and the shaft head partially housed and protected in a suitable seat provided at the free end of the syringe cylinder.

Reference will firstly be made to FIGS. 1 to 3, which show a syringe comprising a hollow cylinder 1 in which an elastic plunger 2 (FIG. 3) is mobile by insertion, and is rigid with one end of a shaft 3, at the other terminal end of which there is provided a shaped head 4 of elongate half-egg shape for operating the shaft and plunger.

A needle 5, such as a hypodermic needle of any known type, is rigid with the lower end of the cylinder.

From FIGS. 1 to 3 it can be seen that the upper free end of the cylinder 1 comprises a socket-shaped enlargement 6 defining a seat dimensioned and shaped in a manner complementary to the lower part of the head 4 (meaning that portion of the end of shaft 3 which is completely outside the cylinder before and while an injection is made, the head 4 also means the end portion of the shaft 3 upon which the finger of the user rests and acts upon injection action), which can thus penetrate practically with no clearance into said seat, as shown in FIG. 3. In this position, i.e. when the plunger 2 has been pushed to the bottom of the cavity in the cylinder 1, a constituent part of the head 4 still projects beyond the upper free edge of the syringe cylinder, but because of the fact that its diameter decreases towards the free end of the head, none of the surface which projects beyond the cylinder can be gripped by the fingers, to pull the shaft and raise the plunger within the cylinder, so that any attempt to use the syringe a second time to draw in new liquid is impossible. In this respect, the free surface of the head 4 is perfectly smooth and free of grippable parts.

The length of the shaft 3 is such that when part of the head 4 has been inserted into the seat in the socket 6 of the cylinder 1, the plunger 2 has reached the bottom of the cylinder cavity, at that end comprising the needle 5.

On the opposing surfaces of the socket 6 and head 4 there are provided (although this is not necessary) an annular recess 7 and an annular rib 8 respectively, these being complementary and being inserted one into the other (FIG. 3) when the head 4 is pressed to the bottom of the seat defined by the socket 6. This further hinders any attempt to withdraw the shaft together with its plunger after the head 4 has been inserted and locked into the seat defined by the end socket 6 of the cylinder, even though the engagement between the recess 7 and the rib 8 is not in fact necessary.

To facilitate the total downward pushing of the shaft, the head 4 is of an elongate shape such that an end portion of the head projects beyond the adjacent surface of the free end portion of the cylinder when the plunger 2 has been pushed to the bottom of the cylinder.

It can easily be seen however that when in this position the head 4 cannot be gripped even with pliers, because of its perfectly smooth surface and its rounded egg shape with a cross-section having a variable surface diameter which is a maximum in proximity to the shaft and gradually reduces towards the free end of the head.

From FIG. 3 it can be seen that it is impossible to operate on the shaft head 4 even with a screwdriver or other tool, as there is no clearance between the head and its seat to allow such an operation.

Figure 4:
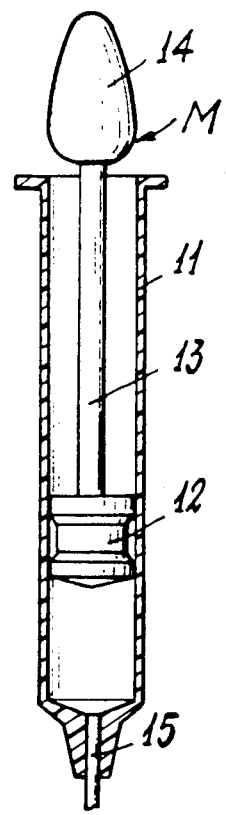
FIG. 4 is a schematic representation of a small-dimensional syringe of the type used for injecting insulin, shown with the shaft head completely free and external to the cylinder.
Figure 5:
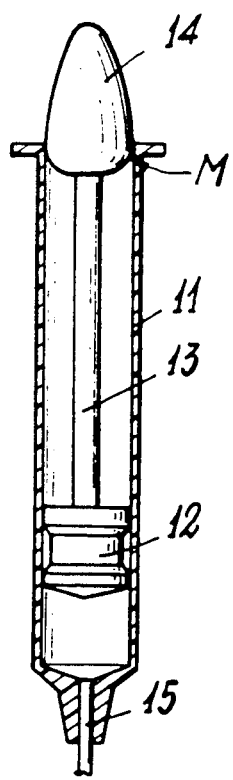
FIGS. 5 and 6 show the same syringe as in FIG. 4, but with the shaft head already engaged in the cylinder cavity, the FIGURES representing the situations somewhat prior to the plunger reaching the bottom of the cylinder and the plunger having reached the bottom of the cylinder respectively.
Figure 6:
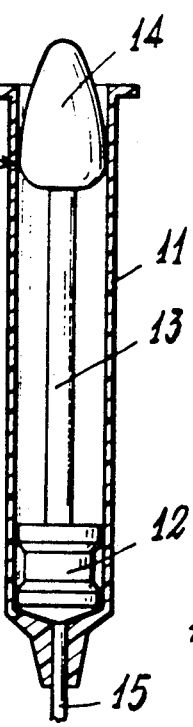

Reference will now be made to FIGS. 4 to 6, which show a small-dimensioned syringe of the type used for injecting insulin and also used by drug addicts to inject heroin into a vein.

This syringe comprises a fairly long but very thin cylinder 11 housing a mobile plunger 12 rigid with the lower end of a shaft 13, the other end of which is rigid with a head 14 of very elongate form, with a cross-section of variable diameter which is a maximum in proximity to the shaft in the region indicated by the arrow M, and gradually reduces towards the free end of the head, the surface of which is perfectly smooth and free from roughness. The lower part of the head 14 is rounded towards the shaft to facilitate insertion of the head into the cavity of the cylinder 11 while injecting the liquid contained in the syringe.

In practice, the head 14 is substantially in the shape of an egg or an ogive elongated in its upper part.

Initially, prior to its use, the syringe is sold in the arrangement shown in FIG. 4, in which the head 14 can be easily gripped with two fingers and pulled to withdraw the plunger 12 from the needle 15 fitted to the cylinder 11, and thus draw liquid into the cylinder, exactly as in the case of similar conventional syringes.

On commencing injection of the liquid, the free end of the head 14 is pressed with a finger. At a certain point the maximum diameter region M of the head becomes positioned within the cylinder 11, immediately below its open end (FIG. 5). The length of the shaft 13 is such that in this situation the plunger 12 has not yet reached the bottom of the cylinder and therefore part of the liquid is still present between the plunger and the cylinder. If an attempt is made to pull the shaft back together with the plunger in order to draw new liquid into the syringe (for the purpose of reusing the syringe), this is found to be impossible because of the smooth tapered form of the head 14.

To inject all the liquid the plunger 12 has to be pushed to the bottom of the cylinder 11 (FIG. 6), causing the head 14 to penetrate deeply into the cylinder cavity, this further movement being defined by the length of the shaft 13.

If a drug addict wished to use the syringe two or more times, he would have to halt the advancement of the plunger within the cylinder at a point in which the head 14 could still be gripped, i.e. with the head higher than the position shown in FIG. 5. However, in such a case a considerable unused quantity of liquid would remain in the syringe, to the extent of certainly discouraging such an attempt.

The maximum diameter of the head at the head region M is preferably slightly greater than the inner diameter of the cylinder, so that the head would have to be slightly forced for its insertion in the cylinder, so making it even more difficult to withdraw the plunger by means of its shaft and head 14 from the position shown in FIGS. 5 and 6.

From the aforegoing it is apparent that the syringe structure is very simple and therefore economical, and that it prevents in an extremely effective manner any attempt to reuse the syringe after the plunger has been pushed beyond a certain limit within the cylinder.

What is claimed as new and desired to be secured by Letters Patent of the United States is:

1. A disposable syringe for once-only use, comprising:
   a hollow cylinder open at one end and connected to a needle at its other end,
   an elongate shaft;
   a plunger slidable under sealed conditions within the cylinder and connected to one end of the elongate shaft, and
   a head having a maximum diameter at least as great as the inner diameter of the cylinder and connected to an opposite, terminal end of the shaft so as to be operable with a finger of a hand of an operator of the syringe, wherein said head is of an elongate form in a length direction of said shaft with a surface diameter of said enlarged head being of varying diameter which is gradually reduced towards the free end of the head, the shaft being of a length such that when the plunger has been pushed to the bottom of the cylinder, the maximum diameter portion of the head passes the open one end of the cylinder and is housed within the cavity of the cylinder.

2. A syringe as claimed in claim 1, wherein said elongate head has its surface shaped as an ogive.

3. A syringe as claimed in claim 1, wherein the maximum diameter of the shaft head is greater than the inner diameter of the cylinder cavity.

4. A syringe as claimed in claim 1, wherein a free end portion of the head is positioned outside the cavity of the cylinder when the plunger is pushed to the bottom of the cylinder.

* * * * *